United States Patent
Sekine et al.

(10) Patent No.: US 11,925,459 B2
(45) Date of Patent: Mar. 12, 2024

(54) MEDICAL SYSTEM CONFIGURED TO DISPLAY SUITABLE POSTURES OF A SUBJECT DURING A MEDICAL PROCEDURE

(71) Applicant: TERUMO KABUSHIKI KAISHA, Tokyo (JP)

(72) Inventors: Yusuke Sekine, Chigasaki Kanagawa (JP); Yuki Sakaguchi, Isehara Shizuoka (JP); Akihiko Tarunaga, Ebina Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 626 days.

(21) Appl. No.: 17/017,553

(22) Filed: Sep. 10, 2020

(65) Prior Publication Data

US 2020/0405194 A1    Dec. 31, 2020

Related U.S. Application Data

(63) Continuation of application No. PCT/JP2019/010537, filed on Mar. 14, 2019.

(30) Foreign Application Priority Data

Mar. 15, 2018 (JP) .................................. 2018-048042

(51) Int. Cl.
*A61B 5/11* (2006.01)
*A61B 5/00* (2006.01)

(52) U.S. Cl.
CPC .......... *A61B 5/1116* (2013.01); *A61B 5/4836* (2013.01); *A61B 5/6847* (2013.01); *A61B 5/7264* (2013.01); *A61B 5/742* (2013.01)

(58) Field of Classification Search
None
See application file for complete search history.

(56) References Cited

U.S. PATENT DOCUMENTS

| 9,873,003 | B2 | 1/2018 | Tsunoo et al. |
| 10,684,691 | B2 | 6/2020 | Hayashi et al. |

(Continued)

FOREIGN PATENT DOCUMENTS

| CN | 103957801 A | 7/2014 |
| CN | 104470583 A | 3/2015 |

(Continued)

OTHER PUBLICATIONS

English Translation of International Search Report dated May 28, 2019, mailed in counterpart International Application No. PCT/JP2019/010537, 1 page.

(Continued)

*Primary Examiner* — Devin B Henson
*Assistant Examiner* — Matthew Eric Ogles
(74) *Attorney, Agent, or Firm* — Kim & Stewart LLP (57) ABSTRACT

A medical system recommends a posture of a subject during a medical procedure. The medical system includes a processor and an output device. The processor determines suitable postures of the subject during the medical procedure based on at least one of subject information, including information on a posture of the subject obtained upon a predetermined movement by the subject and information on the procedure. The output device presents one or more of the suitable postures determined by the processor as recommended postures.

19 Claims, 6 Drawing Sheets

(56) References Cited

U.S. PATENT DOCUMENTS

| | | | |
|---|---|---|---|
| 11,355,232 B2* | 6/2022 | Greiner | G16H 40/20 |
| 2011/0245684 A1* | 10/2011 | Onimura | A61B 5/6852 |
| | | | 600/476 |
| 2011/0263950 A1 | 10/2011 | Larson et al. | |
| 2012/0212582 A1* | 8/2012 | Deutsch | G16H 40/20 |
| | | | 348/46 |
| 2015/0109442 A1* | 4/2015 | Derenne | H04N 7/185 |
| | | | 348/143 |
| 2015/0305612 A1* | 10/2015 | Hunter | A61B 5/061 |
| | | | 600/109 |
| 2017/0140111 A1* | 5/2017 | Karz | G16H 10/60 |
| 2017/0354385 A1* | 12/2017 | Lerch | A61B 6/4435 |
| 2019/0354753 A1* | 11/2019 | Worrall | G06V 40/20 |
| 2020/0311432 A1* | 10/2020 | Greiner | G06V 40/10 |

FOREIGN PATENT DOCUMENTS

| | | | |
|---|---|---|---|
| JP | 2007267773 A | 10/2007 | |
| JP | 2008119517 A | 5/2008 | |
| JP | 2013526900 A | 6/2013 | |
| JP | 2015019777 A | 2/2015 | |

OTHER PUBLICATIONS

English Translation of Written Opinion dated May 28, 2019, mailed in counterpart International Application No. PCT/JP2019/010537, 4 pages.

Office Action dated Apr. 25, 2023 in corresponding Chinese Patent Application No. 201980006944.0, 15 pages (with Translation).

* cited by examiner

| D15 | | | | | | | | |
|---|---|---|---|---|---|---|---|---|
| IDENTIFICATION ID | PATIENT NAME | ADDRESS | AGE | OPERATION HISTORY | HEALTH CONDITION | TARGET LESION | STATE OF TARGET LESION |
| x x x | S | x x x | 25 | PRESENCE | PHYSICAL EXAMINATION RESULT, INTERVIEW RESULT | CORONARY ARTERY | GOOD |
| x x x | T | x x x | 45 | PRESENCE | PHYSICAL EXAMINATION RESULT, INTERVIEW RESULT | FEMORAL VEIN | NORMAL |
| x x x | U | x x x | 33 | ABSENCE | PHYSICAL EXAMINATION RESULT, INTERVIEW RESULT | CEREBRAL ARTERY | NORMAL |
| x x x | V | x x x | 8 | ABSENCE | PHYSICAL EXAMINATION RESULT, INTERVIEW RESULT | CORONARY ARTERY | GOOD |

| MEDICAL INSTITUTION NAME | DOCTOR NAME | PATIENT NAME | DISEASE NAME | SURGICAL PROCEDURE TO BE ADOPTED | SURGICAL TIME | USE DEVICE |
|---|---|---|---|---|---|---|
| A | O | S | x x x x | x x x x | x x x x | x x x x |
| A | P | T | x x x x | x x x x | x x x x | x x x x |
| B | Q | U | x x x x | x x x x | x x x x | x x x x |
| A | R | V | x x x x | x x x x | x x x x | x x x x |

PRESENTATION CONTENT:

| PROCEDURE CONTENT | RECOMMENDED POSTURE | RECOMMENDATION REASON |
|---|---|---|
| 1. PREPARATION PROCEDURE | • BEND WRIST AND ELBOW<br>• HOLD HAND | • CONGESTION OF RADIAL ARTERY FACILITATES CONFIRMATION OF POSITION. |
| 2. INSERTION PROCEDURE | • STRETCH WRIST AND ELBOW | • INSERTABILITY OF MEDICAL DEVICE IS IMPROVED. |
| 3. DELIVERY PROCEDURE | • STRETCH WRIST AND ELBOW | • DELIVERABILITY OF MEDICAL DEVICE IS IMPROVED. |
| 4. TREATMENT PROCEDURE | • BEND A JOINT | • BACKUP POWER OF CATHETER DEVICE IS ENHANCED. |
| 5. HEMOSTASIS PROCEDURE | • STRETCH WRIST AND ELBOW<br>• OPEN HAND | • BURDEN OF SUBJECT IS SUPPRESSED. |

OTHER PRESENTATION CONTENTS

• SUPPORTING POSTURE OF SUBJECT BY WORKING DEVICE DURING PREPARATION PROCEDURE, INSERTION PROCEDURE, DELIVERY PROCEDURE, TREATMENT PROCEDURE IS SUGGESTED.

MEDICAL SYSTEM CONFIGURED TO DISPLAY SUITABLE POSTURES OF A SUBJECT DURING A MEDICAL PROCEDURE

CROSS-REFERENCE TO RELATED APPLICATION(S)

This application is a continuation of International Patent Application No. PCT/JP2019/010537, filed on Mar. 14, 2019, which is based upon and claims the benefit of priority from Japanese Patent Application No. 2018-048042, filed on Mar. 15, 2018, the entire contents of which are incorporated herein by reference.

FIELD

Embodiments relate to a medical system.

BACKGROUND

In the related art, a manipulation of various medical devices introduced into a blood vessel through a puncture site formed in the blood vessel of an arm or a leg of a subject (e.g., patient), and performing a procedure or a treatment for a lesion site is known and is disclosed in Japanese Patent Application No. 2008-119517.

The shape and the current state of a blood vessel may be changed depending on a posture of a subject during a medical procedure. Accordingly, it may be difficult to smoothly perform the medical procedure depending on the posture that the subject takes during the medical procedure. In addition, if the subject is forced into an unnatural posture in order to enable the medical procedure, the burden on the subject would increase.

SUMMARY

In consideration of the above, embodiments provide a medical system which recommends a suitable posture of a subject according to a medical procedure to be performed on the subject.

According to an embodiment, there is provided a medical system including: a processor configured to determine a suitable posture of a subject during a procedure to be performed on the subject based on at least one of subject information, including information on a posture of the subject obtained upon a predetermined movement by the subject and information on the procedure, and an output device configured to present one or more of the suitable postures determined by the processor as recommended postures.

According to embodiments, a more suitable posture among possible postures, that a subject should take during a predetermined procedure is recommended through an output device. A doctor allows the subject to assume the posture recommended through the output device, so that the doctor can smoothly proceed with the procedure. If the procedure is performed on the subject while the subject assumes the posture recommended through the output device, the burden of the subject while the procedure is performed can be reduced.

DETAILED DESCRIPTION OF EMBODIMENTS

Hereinafter, embodiments will be described with reference to the accompanying drawings. In the description of the drawings, the same reference signs are assigned to the same elements, and repeated descriptions are omitted. In addition, dimensional ratios in the drawings are exaggerated for convenience of explanation, and may be different from the actual ratios.

Figure 1:
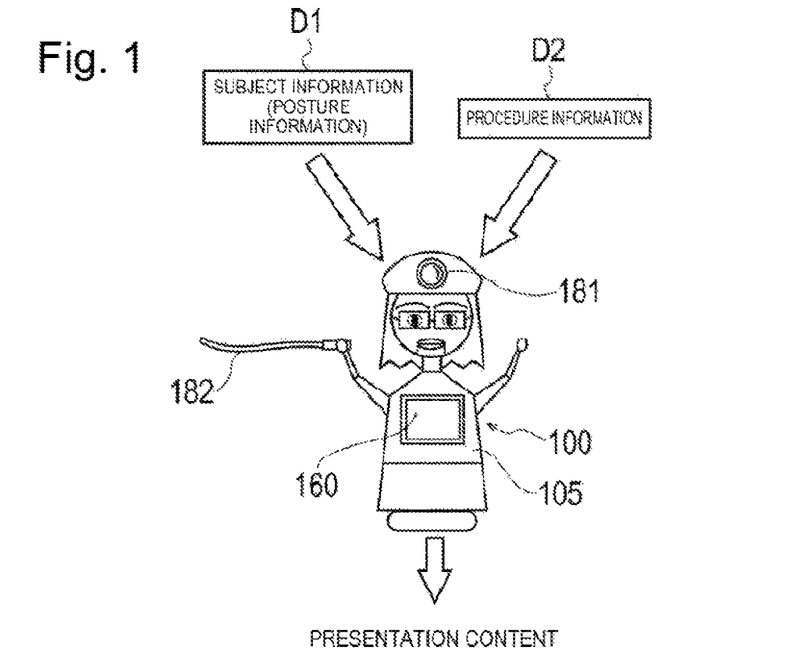
FIG. 1 is a schematic view illustrating an example of a medical system according to the present embodiment.
Figure 2:
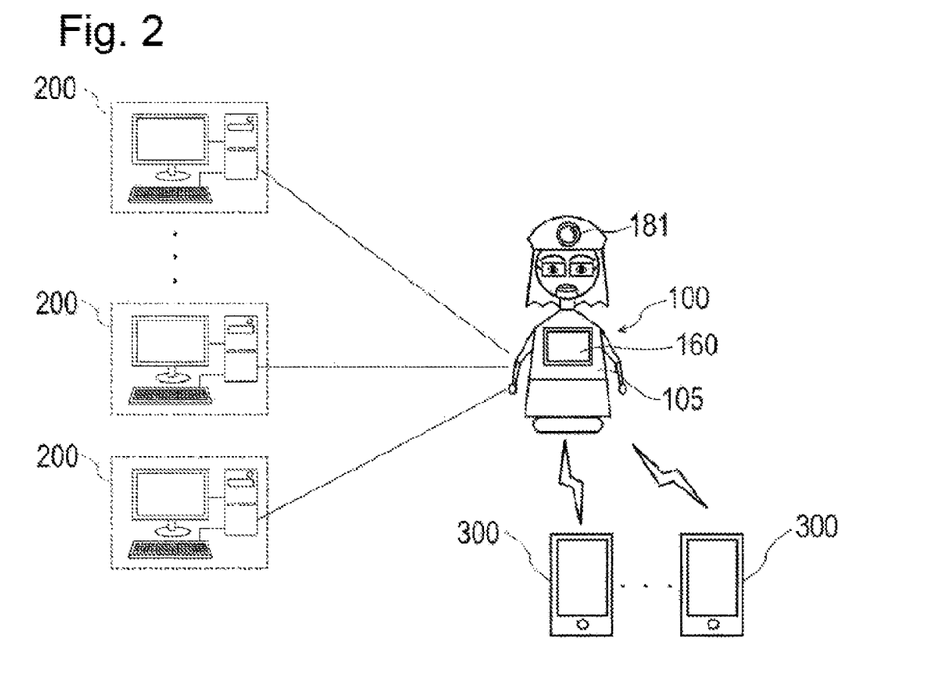
FIG. 2 is a diagram illustrating a network configuration of the medical system according to the present embodiment.
Figure 3:
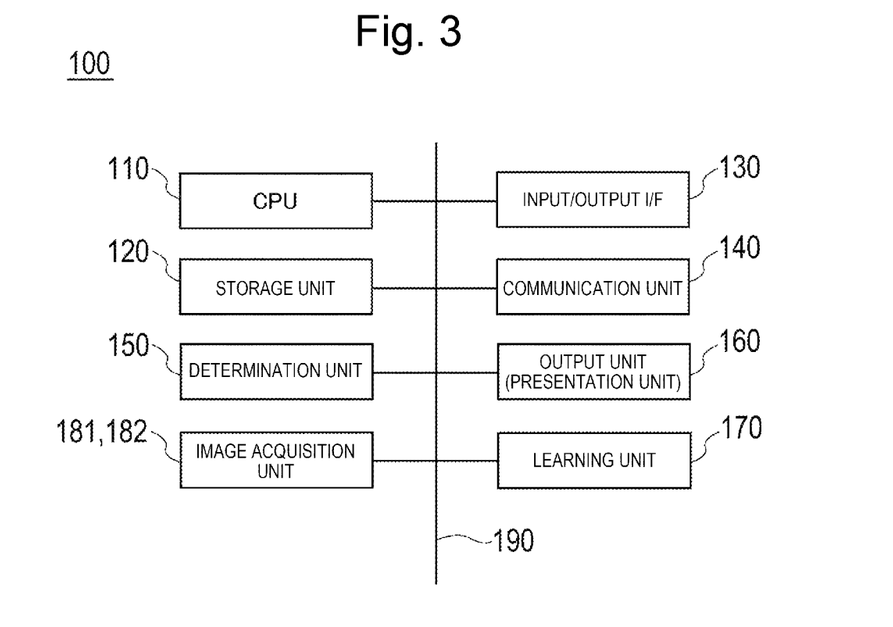
FIG. 3 is a block diagram illustrating a hardware configuration of the medical system according to the present embodiment.
Figure 4:
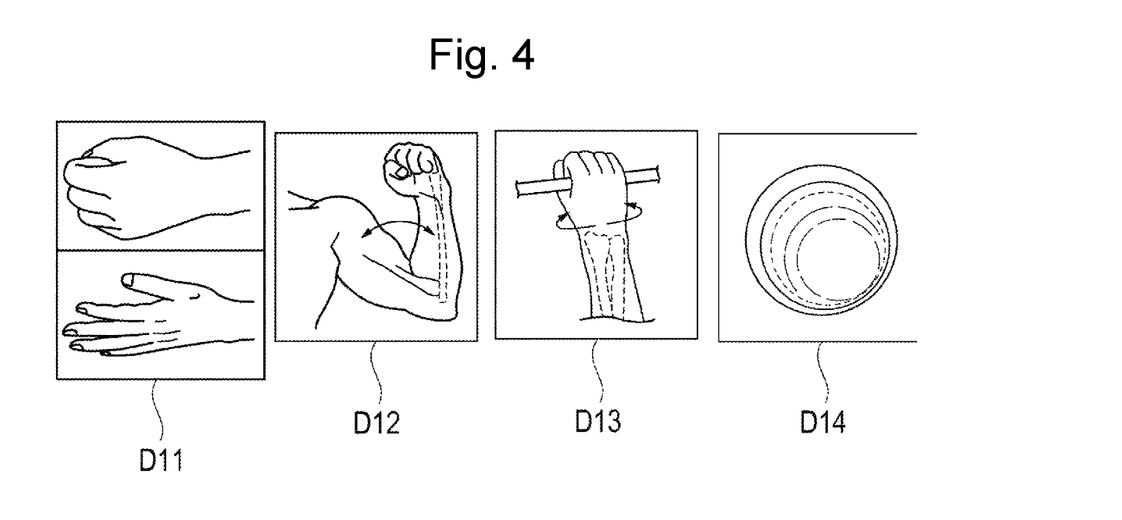
FIG. 4 is a diagram illustrating examples of image information used in the medical system according to the present embodiment.
Figure 5:
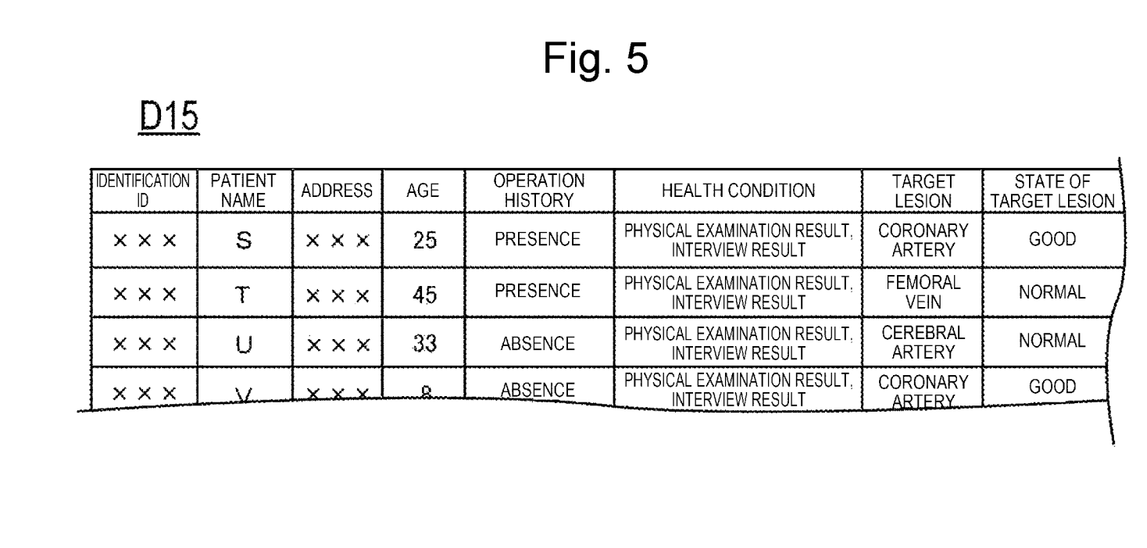
FIG. 5 is a diagram illustrating examples of identification information used in the medical system according to the present embodiment.
Figure 6:
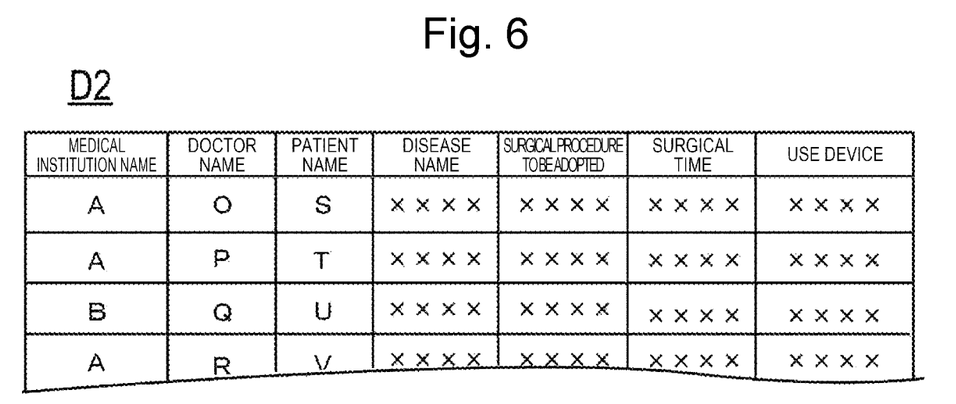
FIG. 6 is a diagram illustrating examples of procedure information used in the medical system according to the present embodiment.
Figure 7:
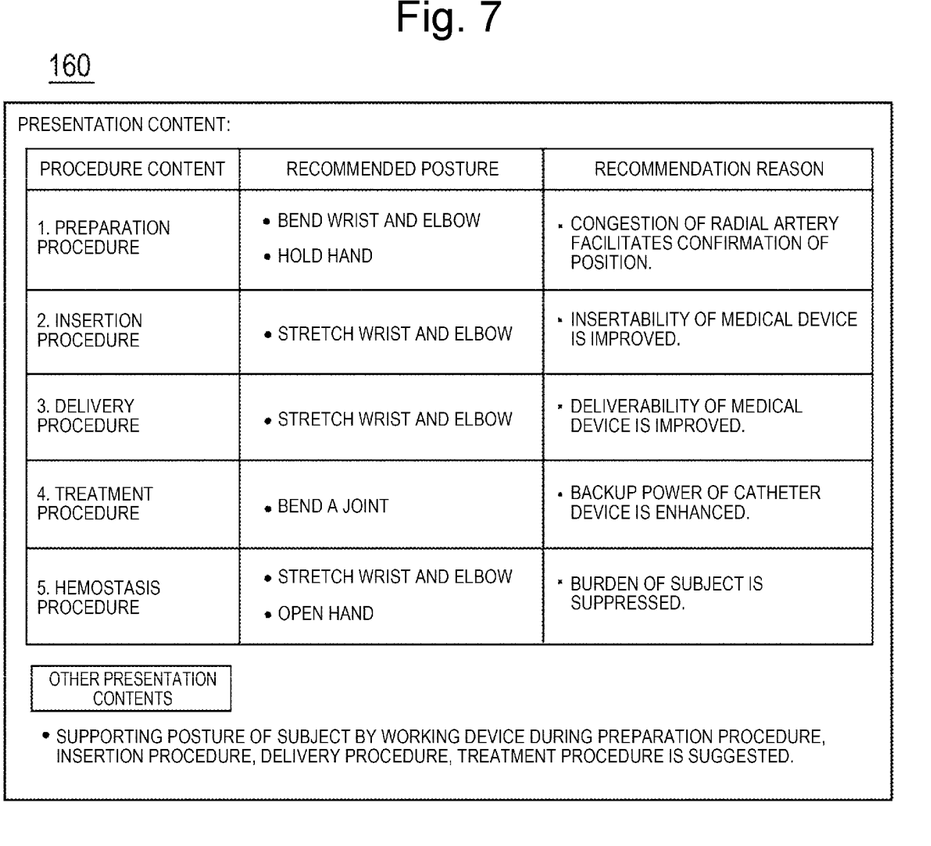
FIG. 7 is a diagram illustrating an example of a presentation content output by the medical system according to the present embodiment.
Figure 8A:
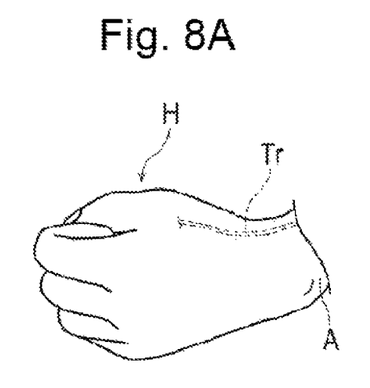
FIG. 8A is a diagram illustrating an example of a hand state while a preparation procedure is performed and FIG. 8B is a diagram illustrating an example of a hand state while an insertion procedure is performed.
Figure 8B:
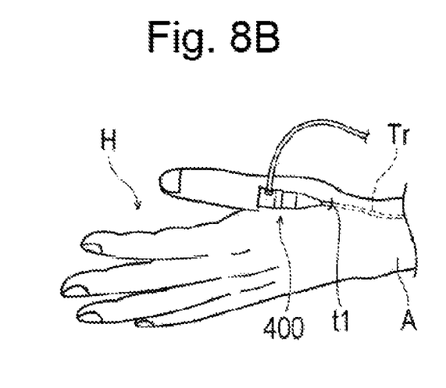

FIGS. 1 and 2 are diagrams for explaining the overall configuration of a medical system 100 according to the present embodiment. FIG. 3 is a diagram for explaining each portion of the medical system 100. FIGS. 4 to 6 are diagrams for explaining data handled by the medical system 100. FIG. 7 is a diagram illustrating an example of a presentation content which is output by the medical system 100. FIG. 8 is a diagram illustrating examples of different hand states during execution of different procedures.

As illustrated in FIG. 1, the medical system 100 is a system which uses subject information D1, procedure information D2, or the like to generate and present a recommended posture of the subject during a procedure.

As illustrated in FIG. 2, the medical system 100 is connected to various medical institution terminals 200 of a medical institution and subject terminals 300 owned by various subjects via a network. In addition, the medical system 100 is also connected to a medical device (for example, a CT device, an operating table, a display monitor, or the like) used during the procedure via a network. The medical system 100 has the function of a server which performs transmission and reception of data between the medical institution terminals 200, the subject terminals 300, and each medical device.

For example, the network can employ a wireless communication method such as WI-FI® or Bluetooth®, other non-contact type wireless communication, or wired communication method.

In the present embodiment, the medical system 100 includes a working device 105 capable of (i) performing communication with a person through dialogue, (ii) holding, transporting, handling an article or the like, and (iii) supporting a procedure. For example, a robot equipped with an AI (artificial intelligence) and having an interactive function can be used as the working device 105.

The working device 105 includes an output unit (also referred to herein as a "presentation unit") 160 having one or more output devices including a display capable of displaying a still image or a moving image and a speaker capable of outputting a voice, a music, or the like. Moreover, the working device 105 includes an image acquisition unit 181 capable of capturing an image of a body of the subject from an outside and an image acquisition unit 182 capable of acquiring a diagnostic image in a blood vessel of the subject.

The external appearance of the working device 105 is not particularly limited, and may be of a humanoid type, an animal type, or the like, for example. The working device 105 can also include a CPU and one or more programs which can be executed by the CPU. The working device 105 does not need to be configured as a robot type device as shown in FIG. 1, and can be a control unit included in a server, that is, as a hardware device that does not have the form of a robot.

In one embodiment, the working device 105 includes a plurality of movable portions. In addition, the working device 105 includes a support portion which supports the arm of the subject and a drive portion which can move the movable portion of the support portion in a predetermined direction. For example, the working device 105 can operate the drive portion in accordance with posture of the subject recommended by the working device 105 in a state where the arm of the subject is placed on the support portion. The working device 105 can cause an elbow of the subject placed on the support portion to bend or stretch. In this way, the working device 105 assists in maintaining or changing the posture of the subject, and thus, it is possible to reduce a work burden of a doctor, a nurse, or the like during the procedure.

Hereinafter, the medical system 100 will be described in detail below.

A hardware configuration of the medical system 100 will be described.

The medical system 100 is not particularly limited, and includes a mainframe or a computer cluster, or the like, for example. As illustrated in FIG. 3, the medical system 100 includes a Central Processing Unit (CPU) 110, a storage unit 120, an input/output I/F 130, a communication unit 140, a determination unit 150, an output unit 160, a learning unit 170, and image acquisition units 181 and 182. The CPU 110, the storage unit 120, the input/output I/F 130, the communication unit 140, the determination unit 150, the output unit (presentation unit) 160, the learning unit 170, and the image acquisition units 181 and 182 are connected to a bus 190, and transmit or receive data or the like via the bus 190.

The CPU 110 executes a control of each unit and various arithmetic processing according to various programs stored in the storage unit 120.

The storage unit 120 includes a Read Only Memory (ROM) which stores various programs or data, a Random Access Memory (RAM) which temporarily stores programs or data as a work area, a hard disk (or other types of nonvolatile storage) which stores various programs and various data including an operating system, or the like.

The input/output I/F 130 is an interface circuit for connecting an input device such as a keyboard, a mouse, a scanner, or a microphone, and an output device such as a display, a speaker, or a printer.

The communication unit 140 is an interface circuit for communicating with the medical institution terminal 200, the subject terminal 300, and various medical devices.

The determination unit 150 is software running on the CPU 110 that determines a suitable posture of the subject in the procedure based on at least one of the subject information D1 and the procedure information D2.

The output unit 160 functions as a presentation unit which outputs the recommendations generated by the medical system 100. For example, the output unit 160 includes a display, a speaker, or the like, through which the recommendations are output. The output unit 160 outputs a recommended posture for each sub-procedure performed during the procedure.

Next, a main function of the medical system 100 will be explained.

The storage unit 120 can store various data such as the subject information D1 and the procedure information D2 on the procedure to be performed on the subject. Moreover, the storage unit 120 can store a program that implements the determination unit 150 which generates the recommendations according to the present embodiment.

The CPU 110 executes the programs stored in the storage unit 120.

Next, the image acquisition units 181 and 182, the subject information D1, and the procedure information D2 will be described.

The subject information D1 includes at least the posture information on the posture of the subject obtained upon a predetermined movement by the subject. The posture information includes image information of the subject acquired when the subject moves.

For example, the image acquisition units 181 and 182 can acquire the image information automatically and regularly or irregularly during the procedure. For example, the image acquisition unit 181 can include an external imaging device 181 which acquires an image captured from outside a body of the subject. For example, the image acquisition unit 182 can include an image acquisition device in the blood vessel which acquires an image captured from an inside of the blood vessel (the inside of the body) of the subject.

For example, the external imaging device 181 includes an X-ray device, a CT device, an MR device, an ultrasound diagnostic apparatus, a camera, or the like, and can acquire external imaging such as an Angio image, a CT image, an MRI image, an ultrasound echo, a still image, and a moving image as the image information.

For example, the image acquisition device 182 in the blood vessel includes an intravascular ultrasound (IVUS) catheter, an image diagnostic catheter such as an optical coherence tomography diagnostic device (OCT catheter), or the like, and acquires a tomographic image inside the blood vessel or the like as the image information.

Before the procedure is performed, the subject takes a predetermined posture, the external imaging device 181 photographs the posture, and a state of the blood vessel while the subject is in the predetermined posture is photographed with the image acquisition device 182 in the blood vessel. FIG. 4 illustrates the image information D11, D12, D13, and D14. The image information D11 shows a state (holding state, open state) of a hand of the subject, the image information D12 shows a state where an elbow is bent, and the image information D13 shows the external imaging (still image) of a wrist in a state of being twisted. The image information D14 shows a tomographic image of the inside of the blood vessel while the subject has assumed a predetermined posture.

For example, the image information is transmitted directly from the image acquisition units 181 and 182 or indirectly by an input work of a health care worker such as a nurse. Moreover, the image information can also be acquired from the medical institution terminal 200 or the subject terminal 300.

For example, the subject information D1 includes identification information D15 which identifies the subject. For example, as illustrated in FIG. 5, the identification information D15 includes identification ID of the subject, a patient name (subject name), an address, an age, a past operation history, a health condition, a name of a target lesion which is a target of this procedure, and data regarding a state of the target lesion. For example, the data regarding the operation history, the health condition, and the state of the target lesion can be acquired from an electronic medical chart or the like. For example, the data regarding the state of the target lesion can include data regarding a current state of the blood vessel when the procedure target is the blood vessel. The data regarding the current state of the blood vessel can be obtained from the doctor determining the current state of the blood vessel from the tomographic image or the like of the interior of the blood vessel. The tomographic image or the like of the interior of the blood vessel is selected from the image information acquired prior to the procedure. Moreover, for example, the state of the target lesion includes a stenosis degree of stenosed site and a characteristic (e.g., hardness of a blood vessel wall, or the like) of the target lesion in a case where a disease to be treated is a coronary artery stenotic lesion or the like.

For example, the state of the target lesion includes an amount of bone and an amount of muscle of the subject, or the like. In a big-boned and muscular subject, a movement involving the bending or twisting of a joint causes a blood vessel to be compressed or bent quite significantly. Therefore, even in the same posture, the big-boned and muscular subject needs to take a gentle posture compared to a subject having less bone mass and less muscle. Moreover, the age of the subject also can be used as a factor. An elderly person is easily subjected to fatigue fracture from long-term bending. Therefore, it is possible to reduce the burden on the subject by favoring a gentle posture instead of an extreme posture.

The identification information D15 can also include data regarding a medical history of the patient, medical history of family members, data from a physical examination result (height, weight, blood pressure), or the like. Moreover, for example, the identification information D15 can also include genetic information of the subject. The genetic information may include not only the genetic information of the subject but also genetic information of blood relatives. For example, the genetic information can be determined from a DNA test result. For example, when a disease of the subject is determined, the genetic information can be used to determine whether or not the disease may be genetic.

As illustrated in FIG. 6, for example, the procedure information D2 includes data regarding a name of a medical institution, a name of a doctor who will be in charge of a surgery, a patient name (subject name), a disease name, a surgical procedure to be adopted in the surgery, and a planned surgery time, and a use device. For example, the data regarding the use device includes information on a type of an introducer inserted into the blood vessel, a type of a guide wire, a type of a treatment device, or the like.

In addition, for example, the storage unit 120 may store "general anatomical information" (data regarding anatomical information, which does not take into consideration the specific anatomical features of the subject) and "general recommended posture information" (data on the recommended posture selected without considering the anatomical features of the subject). For example, the determination unit 150 can compare the subject information D1 with the general anatomical information to determine the presence or absence of an anatomical feature specific to the subject. Moreover, the determination unit 150 can determine whether or not to present the recommended posture based on the general recommended posture information while referring to the determined anatomical feature of the subject. In a case where the anatomical feature specific to the subject is detected, the presentation unit 160 presents the recommended posture that reflects the difference between the specific anatomical feature of the patient and the general recommended posture information. As described above, the medical system 100 compares the general anatomical information with the anatomical information in which the anatomical feature specific to the subject is considered, and it is possible to select the recommended posture in various procedures based on a difference of the comparison results (for example, if the comparison results are structural features of the blood vessel, a position of the blood vessel branch, or the like). Therefore, the medical system 100 can reduce a processing burden (burden required for the calculation processing) required for selecting the recommended posture.

Moreover, the posture information D1 can also include body pressure data regarding a body pressure applied to the body of the subject. The body pressure data is data on the body pressure applied to the subject when the subject lies on a bed or the like. For example, the body pressure data can be acquired by a pressure sensor attached to a portion such as a bed, a surgical garment worn by the subject, or the like which comes into contact with an elbow, a shoulder, a waist, or the like. The determination unit 150 can determine a posture which reduces a risk of the subject generating a pressure ulcer, based on the body pressure data. The presentation unit 160 can present the posture which reduces the risk of the subject generating the pressure ulcer. A health care worker such as a nurse or a doctor causes the subject to take the posture recommended by the presentation unit 160, and thus, it is possible to appropriately prevent the subject from generating the pressure ulcer. Note that the presentation unit 160 can present a posture in which the body pressure applied to the subject is less than 40 mmHg, for example.

Next, the learning unit 170 will be described. The learning unit 170 is machine learning software running on the CPU 110 that performs machine learning using the subject information D1 and the procedure information D2. In the present specification, the "machine learning" refers to analyzing input data using an algorithm, extracting a useful rule, a determination criterion, or the like from an analysis result, and developing the algorithm.

The medical system 100 according to the present embodiment performs the machine learning based on the subject information D1 and the procedure information D2 obtained during the procedure in order to assist the doctor while the doctor performs the procedure, and presents the recommended posture of the subject in real time. In this case, the recommended posture of the subject is comprehensively determined from past results and the latest information obtained from hospital or various cases. The presentation of the recommended posture of the subject is not limited to presenting one optimal posture, and a plurality of postures may be listed as candidates for the recommended posture of the subject.

Specifically, the output unit 160 of the medical system 100 presents the posture of the subject recommended at present in real time in consideration of the progress made during the procedure when there is a request from a doctor, a nurse, or the like during the procedure, or when it is recommended to present the result of the machine learning even if there is no request made during the procedure. Moreover, when the output unit 160 presents the recommended posture of the subject, the output unit 160 shows the reason for making the recommendation together with the presentation content. When there are a plurality of reasons, the plurality of reasons can be presented. The output unit 160 shows the reason for recommending the posture of the subject together with the posture of the subject, and thus, a doctor, a nurse, or the like may adopt the recommendation with confidence. For example, the reason may be presented by showing a relationship between the data using a graph or a table, or specifically showing an event which is a factor leading to the reason together with a number, such as a contribution rate.

An example of the presentation content will be described with reference to FIGS. 7 and 8.

The presentation content output by the medical system 100 includes the content of the procedure and the recommended posture of the subject. For example, the content of the procedure includes a preparation procedure for preparing to introduce the medical device into the subject, an insertion procedure for inserting the medical device through a puncture site of the subject, a delivery procedure for delivering a treatment device to a desired position within the blood vessel through the puncture site, a treatment procedure for performing a predetermined procedure in a blood vessel by the treatment device, a hemostasis procedure in which hemostasis is performed on the puncture sites, or the like. For example, the recommended posture of the subject includes a posture in which a wrist or an elbow is bent, a posture in which the wrist or the elbow is stretched, a posture in which a hand is held in a closed position, and a posture in which a hand is opened. The recommended posture of the subject may include a bending angle of the wrist or elbow.

In the following, as an example of presentation content output by the medical system 100, a procedure will be described. In this procedure, the medical device 400 such as an introducer is inserted into a radial artery Tr (radial artery or distal radial artery which runs near a snuff box) which runs from a palm artery of a hand H of the subject to an arm side, and is delivered to a lesion site to perform a treatment.

First, in the preparation procedure, preparation is performed to puncture a puncture needle in the radial artery Tr running in the hand H of the subject. Next, in the insertion procedure, the medical device 400 is inserted into the radial artery Tr via a puncture site t1 formed in the hand H of the subject. Next, a predetermined treatment device is delivered to a desired position in the blood vessel via the medical device 400. Next, in the treatment procedure, a predetermined procedure is performed in the blood vessel by the treatment device. Lastly, in the hemostasis procedure, hemostasis is performed on the puncture site t1 formed on the dorsal side of the hand H of the subject.

As illustrated in FIG. 7, the output unit 160 presents the recommended posture of the hand of the subject for each of the preparation procedure, the insertion procedure, the delivery procedure, the treatment procedure, and the hemostasis procedure.

For example, the output unit 160 presents "bending a wrist and elbow" and "holding a hand" as the recommended posture during the preparation procedure. The output unit 160 presents "congestion of the radial artery Tr facilitates confirmation of the (puncture) position" as the reason for making the recommendation. As illustrated in FIG. 8A, the hand H is held in a state where a wrist A is bent, and thus, the radial artery Tr can be congested and expanded, and can be raised from the surface of the hand H. Accordingly, the doctor can easily confirm the position of the radial artery Tr.

The output unit 160 presents "stretching the wrist and elbow" as the recommended posture during the insertion procedure. The output unit 160 presents "insertability of the medical device is improved" as the reason for making the recommendation. As illustrated in FIG. 8B, the hand H is open a state where the wrist A is stretched, and thus, the radial artery Tr is straightened, and the insertability of the medical device 400 is improved.

The output unit 160 presents "stretching the wrist and elbow" as the recommended posture during the delivery procedure. The output unit 160 presents "deliverability of the medical device is improved" as the reason for making the recommendation.

The output unit 160 presents "bending a joint" as the recommended posture during the treatment procedure. The output unit 160 presents "backup power of a catheter device is enhanced" as the reason for making the recommendation.

The output unit 160 presents "stretching the wrist and elbow" and "opening the hand" as the recommended posture during the hemostasis procedure. The output unit 160 presents "a burden of the subject is suppressed" as the reason for making the recommendation.

For example, the output unit 160 presents "supporting the posture of the subject by the working device 105 during the preparation procedure, the insertion procedure, the delivery procedure, the treatment procedure is suggested" as other presentation contents. For example, when the medical system 100 presents the working device 105 to do the work for supporting, the working device 105 itself operates to automatically perform the work for supporting the posture of the subject. The working device 105 may start the work after receiving the input from the doctor or the nurse, or may present a prompt for the nurse or the like to perform the work. Moreover, for example, when the working device 105 automatically performs the work for supporting, the working device 105 may select and perform only a posture having a high degree of recommendation to be performed out of a plurality of presented postures of the subject.

The doctor selects the posture of the subject based on the contents output by the medical system 100, and proceeds with the procedure. The medical system 100 newly acquires various data (subject information D1, procedure information D2) acquired while the doctor proceeds with the procedure according to the posture of the subject selected by the doctor, and appropriately presents a new posture of the subject during the procedure. Further, the learning unit 170 can perform the machine learning using updated data and update a learning model. Moreover, various data obtained by the procedure performed by the doctor can be stored as new data and used for the procedure after the next time.

As described above, the medical system 100 according to the present embodiment includes the determination unit 150 which determines the suitable posture of the subject in the procedure to be performed on the subject based on at least one of the subject information D1 including the posture information on the posture of the subject obtained upon a predetermined movement by the subject and procedure information D2 on the procedure, and the output unit (presentation unit) 160 which presents the recommended posture in the procedure out of the postures determined by the determination unit 150.

The medical system 100 presents a more suitable posture out of the postures that the subject should take during a predetermined procedure, through the output unit (presentation unit) 160. The doctor allows the subject to assume the posture recommended through the output unit 160, and thus, the doctor can smoothly proceed with the procedure. In addition, the subject receives the procedure at the posture recommended through the output unit 160, and thus, the subject can reduce the burden of the subject while the procedure is performed. In particular, since a standard protocol (for example, the procedure, the recommended posture of the subject, or the like) is not well established in the insertion of the medical device 400 from the puncture site t1 formed in the hand H of the subject into the radial artery Tr or the insertion or various treatments of the treatment device via the medical device 400, the support by the medical system 100 is very effective.

Hereinbefore, the medical system according to the present invention has been described through the embodiments. However, the present invention is not limited to each configuration described in the specification, and may be appropriately changed based on the language of the claims.

For example, as the example of the procedure supported by the medical system, the example of inserting the medical device from the radial artery running a hand or the example of the treatment using a predetermined treatment device is described. However, the content of the procedure is not particularly limited thereto. Moreover, the image or the like captured in a blood vessel is described as the example of the image information. However, the image information can be appropriately changed according to the content of the procedure, an organ to be treated, or the like.

In addition, the means and method for performing various processes in the medical system according to the embodiment can be realized by any one of a dedicated hardware circuit and a programmed computer. Moreover, for example, the program running in the CPU may be provided by a computer-readable recording medium such as a Compact Disc Read Only Memory (CD-ROM), or may be provided online via a network such as the Internet. In this case, in general, a program recorded on the computer-readable recording medium is transferred to and stored in a storage unit such as a hard disk. Further, the program may be provided as a stand-alone application software.

What is claimed is:

1. A medical procedure support system comprising:
   one or more imaging devices;
   a storage device that stores information on recommended postures to be taken by a subject during a medical procedure including a plurality of sub-procedures;
   a display device; and
   a processor configured to:
      control the imaging devices to capture images and store the captured images in the storage device,
      during the medical procedure, determine one or more suitable postures of the subject to be taken in each of the sub-procedures based on images of the subject taking different postures that have been captured by the imaging devices and stored in the storage device and the stored information on the recommended postures, and
      generate a screen to be displayed on the display device, the screen indicating each of the sub-procedures and the determined suitable postures corresponding to said each of the sub-procedures, wherein
   the captured images include an image acquired inside a body of the subject.

2. The medical procedure support system according to claim 1,
   wherein the captured images include an image acquired outside the body of the subject.

3. The medical procedure support system according to claim 2,
   wherein the storage device stores general anatomical information regarding the subject,
   wherein the processor is configured to determine an anatomical feature specific to the subject based on the general anatomical information, and
   wherein the processor determines the suitable postures further based on the determined anatomical feature.

4. The medical procedure support system according to claim 3,
   wherein the processor determines the suitable postures of a hand of the subject to be taken in an insertion procedure, which is one of the sub-procedures.

5. The medical procedure support system according to claim 3,
   wherein the processor determines the suitable postures of a hand of the subject to be taken in each of a delivery procedure, a treatment procedure, and a hemostasis procedure that are ones of the sub-procedures.

6. The medical procedure support system according to claim 5,
   wherein the storage device stores body pressure data regarding a body pressure applied to the body of the subject, and
   wherein the processor determines the suitable postures which reduce a risk of the subject generating a pressure ulcer, based on the body pressure data.

7. A medical system comprising:
   a robot including:
      a display device, and
      a processor programmed to:
         acquire information on recommended postures to be taken by a subject during a medical procedure including a plurality of sub-procedures,
         control one or more imaging devices to capture images,
         during the medical procedure, determine one or more suitable postures of the subject to be taken in each of the sub-procedures based on images of the subject taking different postures that have been captured by the imaging devices and the acquired information on the recommended postures, and
         generate a screen to be displayed on the display device, the screen indicating each of the sub-procedures and the determined suitable postures corresponding to said each of the sub-procedures, wherein
   the imaging devices include a first imaging device for capturing a first image of an interior of the body of the subject that shows a treatment location for the medical procedure.

8. The medical system according to claim 7, wherein said one or more suitable postures determined for at least one of the sub-procedures of the medical procedure include two different suitable postures.

9. The medical system according to claim 8, wherein the sub-procedures include a preparation procedure, an insertion procedure, a delivery procedure, a treatment procedure, and a hemostasis procedure.

10. The medical system according to claim 7, wherein the imaging devices further include a second imaging device for capturing a second image of an exterior of a body of the subject.

11. The medical system according to claim 10, wherein the second image shows a posture of a hand and a wrist of the subject, and the treatment location for the medical procedure shown in the first image is an interior of a blood vessel of the subject.

12. The medical system according to claim 10, wherein the second imaging device captures the second image when the subject moves.

13. The medical system according to claim 7, wherein the suitable postures are determined further based on an amount of bone mass and muscle mass of the subject and an age of the subject.

14. The medical system according to claim 7, wherein the processor is further programmed to execute machine learning to recommend one of the suitable postures based on prior selections that were made among suitable postures for the same medical procedure.

15. A method of presenting one or more suitable postures of a subject during a medical procedure to be performed on the subject, said method comprising:
 storing, in a storage device, information on recommended postures to be taken during the medical procedure including a plurality of sub-procedures;
 before the medical procedure is performed on a subject, controlling one or more imaging devices to capture images of the subject taking different postures, and storing the captured images in the storage device;
 during the medical procedure, determining one or more suitable postures of the subject to be taken in each of the sub-procedures based on the stored images and the stored information; and
 generating a screen to be displayed on a display device, the screen indicating each of the sub-procedures and the determined suitable postures corresponding to said each of the sub-procedures.

16. The method according to claim 15, further comprising:
 capturing a first image of an exterior of a body of the subject and
 capturing a second image of an interior of the body of the subject that shows a treatment location for the medical procedure.

17. The method according to claim 16, wherein the first image shows a posture of a hand and a wrist of the subject, and the treatment location for the medical procedure shown in the second image is an interior of a blood vessel of the subject.

18. The method according to claim 15, wherein the suitable postures are determined further based on an amount of bone mass and muscle mass of the subject and an age of the subject.

19. The medical procedure support system according to claim 1, wherein the processor determines the suitable postures further based on an amount of bone mass and muscle mass of the subject and an age of the subject.

* * * * *